United States Patent [19]

Kaspi et al.

[11] 4,254,029
[45] Mar. 3, 1981

[54] PROCESS FOR PREPARING β-LACTAM ANTIBIOTICS

[75] Inventors: Joseph Kaspi, Givataim; Moshe Gross; Menasse Nussim, both of Netanya, all of Israel

[73] Assignee: Plantex Ltd., Netanya, Israel

[21] Appl. No.: 95,164

[22] Filed: Nov. 19, 1979

[30] Foreign Application Priority Data

Nov. 20, 1978 [JP] Japan ................................ 53-144027
Jun. 25, 1979 [IL] Israel ................................ 54-57635

[51] Int. Cl.³ .................. C07D 501/06; C07D 499/12
[52] U.S. Cl. .................................. 260/239.1; 544/24; 544/26; 544/21; 544/30
[58] Field of Search ................ 544/25, 30, 26, 21, 544/27, 28, 16; 260/239.1

[56] References Cited

U.S. PATENT DOCUMENTS 3,694,437  9/1972  Jackson ............................. 544/30
3,933,810  1/1976  Leustedt ........................... 544/30

*Primary Examiner*—Nicholas S. Rizzo
*Attorney, Agent, or Firm*—Hubbell, Cohen, Stiefel & Gross

[57] ABSTRACT

Compounds of formula (I):

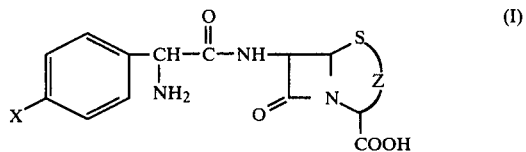

[in which:

Z represents a group of formula

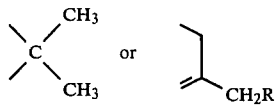

R represents a hydrogen atom, a 1-pyridyl group or a group of formula —YR' (in which: R' represents an alkyl group, an alkanoyl group a carbamoyl group or a heterocyclic group; and Y represents an oxygen or a sulphur atom);

X represents a hydrogen atom or a hydroxy group; and the α-amino acid moiety is in the D(—) configuration]

are prepared by silylating the corresponding compound having an amino group at the 6-penam or 7-cepham position, acylating the silylated compound with D(—)-p-hydroxyphenglycyl chloride hydrochloride or D(—)-p-hydroxyphenylglycyl chloride hydrochloride and then hydrolyzing the acylated product. By carrying out the reaction in the presence of an N-alkylpyrrolidone, it is possible to improve the yields and purity of the desired product.

20 Claims, No Drawings

PROCESS FOR PREPARING β-LACTAM ANTIBIOTICS

The present invention relates to an improved process for the preparation of certain β-lactam antibiotics, specifically penicillin and cephalosporin derivatives.

The β-lactam compounds to which the process of the invention is applicable are compounds of formula (I):

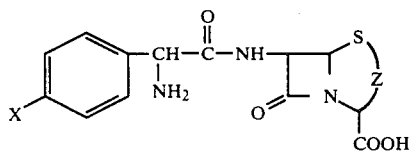

in which:

Z represents a group of formula

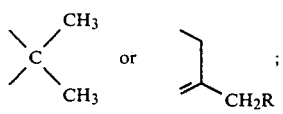

R represents a hydrogen atom, a 1-pyridyl group or a group of formula —YR' (in which: R' represents an alkyl, preferably methyl, group, an alkanoyl group, a carbamoyl group or a heterocyclic group; and Y represents an oxygen or a sulphur atom);

X represents a hydrogen atom or a hydroxy group; and the α-amino acid moiety in the α-aminophenylacetamido side chain is in the D(—) configuration.

Compounds of formula (I) are well-known and these compunds, as well as salts and esters thereof, are well-known to have broad spectrum antibacterial activity and they are widely used as antibacterial drugs, particularly for oral administration.

Many processes are known for the preparation of these compounds, the majority of such processes which are of industrial value involve, in principle, the acylation of 6-aminopenicillanic acid (6-APA), 7-aminocephalosporanic acid (7-ACA) or a derivative thereof with an α-aminophenylacetic acid or a substituted α-aminophenylacetic acid, forming a peptide linkage. However, the 6-APA or 7-ACA and the substituted or unsubstituted α-aminophenylacetic acid are amino-acids and thus several different peptide bonds could be formed. In order to eliminate undesired condensation reactions, the amino group of the substituted or unsubstituted α-aminophenylacetic acid should be blocked and its carboxyl group should be activated prior to the condensation reaction. This ensures that only compounds of formula (I) are formed. This protection of the amino group and activation of the carboxyl group are widely described in the literature of peptide chemistry, for example, M. Goodman and G. W. Kenner, Adv. Protein Chem. 12, 465 (1957), T. Wieland and H. Determann, Angew. Chem. Internat. Ed., 2, 358 (1963) and A. Kapoor, J. Pharm. Sci., 59, 1 (1970).

The protection of the amino group is usually effected by means of a group which is stable under the conditions of the acylation reaction but which can easily be removed subsequently. The need for easy removal is dictated by the sensitivity of the β-lactam ring in the product. The activation of the carboxyl group is usually achieved by its conversion to an acyl halide or to an active mixed anhydride.

One of the main processes in the manufacture of α-aminopenicillins uses the acylation of 6-APA with the acyl chloride hydrochloride of the appropriate α-aminoarylacetic acid. This process has the advantages that the acid chloride is easily obtained in pure form and the amino-protecting group (the hydrochloride group) is easily removed by adjusting the pH of the reaction mixture. The use of such acyl chloride hydrochlorides has been discloses, for example, in U.K. Patent Specification No. 938,321 under anhydrous conditions and in U.K. Patent Specification No. 962,719 in cold aqueous acetone. However, these methods produce relatively impure products containing degradation and polymerization by-products. As a result, improved methods for isolating and purifying such penicillins via β-naphthalenesulphonates or sodium bis(2-ethylhexyl)sulphosuccinate have been developed.

The acid chloride hydrochloride method is generally not carried out in an aqueous medium, as the water would, to some extent, decompose the reactive acid chloride before it has an opportunity to react with the 6-APA. In organic solvents, however, the limited solubility of the 6-APA necessitates the use of large volumes of reaction mixture. This has led to the wide use of silyl esters of 6-APA to protect its carboxyl group and to enhance the solubility of the 6-APA in organic solvents, such as chlorinated hydrocarbons. The use of trialkylsilyl esters has been disclosed, for example, in Ann., 673, 166 (1964). U.K. Patent Specification No. 1,008,468, U.K. Patent Specification No. 959,853, U.K. Patent Specification No. 964,449, U.S. Pat. No. 3,249,622 and U.K. Patent Specification No. 1,339,605.

The usual technique is to react 6-APA with a silylating agent in an organic solvent and then condense the silylated product with the acyl chloride hydrochloride of the α-aminoarylacetic acid. The condensation is carried out in the presence of a weak amine, which serves to neutralize the hydrochloric acid generated by the reaction.

The weak amine used in this step should be strong enough to capture all of the hydrochloric acid formed; if all of the acid is not neutralized, it will react with unreacted silylated 6-APA and produce a species which is unreactive towards acylation. On the other hand, the weak amine should be less basic than the amino group of the α-aminoarylacetic acid, since this group will otherwise be deprotected and undesired products will be formed. The most common bases used for this purpose are N,N-dimethylaniline and quinoline; however, these amines have a high toxicity. The final products [the compounds of formula (I)] are always contaminated by these toxic amines and the health regulations of many countries prohibit the administration of such contaminated products and require that they be first subjected to complicated purification procedures.

German Offenlegungsschrift No. 2,701,407 has proposed the use as acid acceptor of amides of formula $R_1CONHR_2$, in which $R_1$ represents a $C_1$-$C_6$ alkyl group, an aralkyl group or an amino group having one or two $C_1$-$C_6$ alkyl substituents, and $R_2$ represents a hydrogen atom, a $C_1$-$C_6$ alkyl group or an aralkyl group. Although the toxicity of these amides is less than that of the aromatic amines hitherto used, it is still not satisfactory.

Attempts have been made to carry out the process using dialkylacetamides (i.e. the compounds used in the German Offenlegungsschrift but with the hydrogen atom replaced by an alkyl group); however, the process using these compounds as acid acceptors does not work.

Similar processes have been proposed for the preparation of corresponding cephalosporin derivatives and similar difficulties have been encountered. Examples of processes which have been proposed for the preparation of cephalosporin derivatives appear in Canadian Pat. No. 1,018,516 and in U.S. Pat. No. 3,843,637.

There is, therefore, a need for a process for producing compounds of formula (I) of high purity, but without the disadvantages of the known processes.

We have now surprisingly found that N-alkylpyrrolidones can be used as acid acceptors in the production of compounds of formula (I). N-alkylpyrrolidones are known compounds which are widely used in many pharmaceutical compositions, mostly in polymeric form. The usefulness of N-alkylpyrrolidones as acid acceptors is the more surprising since the corresponding process carried out with tertiary dialkylacetamides does not work.

Unlike the compounds hitherto used as acid acceptors, N-alkylpyrrolidones are not amines, but they are cyclic amides. Their use offers several advantages: they are weak bases but still sufficiently basic to neutralize the acid formed in the acylation reaction; they are miscible with water in all proportions and thus are easily removed from the product by washing it with water (this is not the case with aromatic amines at non-acidic pH values); as a result, a very pure product is obtained. Moreover, the toxicity of the N-alkylpyrrolidones is extremely low—data available on N-methylpyrrolidone showed an oral $LD_{50}$ of 7.5 g/kg in rats. As a result, the use of N-alkylpyrrolidones as acid acceptors allows a purer and safer material to be produced.

Thus, the present invention consists in a process for the preparation of a compound of formula (I), as defined above, which comprises:

(a) silylating a compound of formula (II):

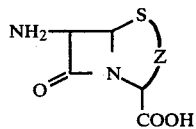

(II)

(in which Z is as defined above);
(b) acylating the product of step (a) with D(−)-phenylglycyl chloride hydrochloride or with D(−)-p-hydroxyphenylglycyl chloride hydrochloride in the presence of an N-alkylpyrrolidone, the molar ratio of said N-alkylpyrrolidone to said compound of formula (II) being from 1:1 to 4:1; and
(c) hydrolyzing the product of step (b) to give said compound of formula (I).

The silylating agent employed in step (a) is preferably an alkylchlorosilane, an alkoxychlorosilane or hexaalkyldisilazane; in these compounds, the alkyl groups preferably have from 1 to 4 carbon atoms and, where the silylating agent contains two or more alkyl groups, the alkyl groups are preferably the same. Preferred alkylchlorosilanes are trialkylchlorosilanes (e.g. chlorotrimethylsilane) or dialkyldichlorosilanes (e.g. dichlorodimethylsilane). An example of a suitable alkoxychlorosilane is triethoxychlorosilane and an example of a suitable hexaalkyldisilazane is hexamethyldisilazane.

Step (a) will normally be carried out in the presence of an inert, normally organic, solvent. Since the same solvent will preferably be used throughout the whole of the process of the invention, it is preferably a solvent in which the reagents and the end products are soluble but which does not react with the reagents or the end product. Preferred solvents are chlorinated hydrocarbons (e.g. methylene chloride) or acetonitrile.

The N-alkylpyrrolidone used as acid acceptor in step (b) is preferably N-methylpyrrolidone; however, higher N-alkylpyrrolidones can be employed, for example N-propylpyrrolidones. The preferred ratio of N-alkylpyrrolidone to compound of formula (II) is from 1.8:1 to 2.2:1.

The hydrolysis in step (c) of the process of the invention is preferably carried out simply by adding water to the reaction mixture; if a separate organic layer forms, this may be separated. The desired compound of formula (I) may be separated from the reaction mixture by conventional means. For example, the pH of the reaction mixture may be adjusted to the isoelectric point or to approximately the isoelectric point of the desired compound to precipitate it and the precipitate may then be separated, e.g. by filtration or centrifugation. If desired, the compound thus obtained may be further purified by conventional means, e.g. recrystallization or chromatography.

The process of the present invention, in a preferred embodiment, thus consists of the following steps:
(i) silylating a compound of formula (II) with an alkylchlorosilane, an alkoxychlorosilane or a hexaalkyldisilazane in an inert solvent;
(ii) adding an N-alkylpyrrolidone to the reaction mixture, the molar ratio of N-alkylpyrrolidone to compound of formula (II) being from 1:1 to 4:1;
(iii) reacting D(−)-phenylglycylchloride hydrochloride or D(−)-p-hydroxyphenylglycyl chloride hydrochloride with the product of step (ii);
(iv) hydrolyzing the product of step (iii) with water and, if necessary, separating the organic phase;
(v) adjusting the pH of the reaction mixture at or about the isoelectric point of the desired compound of formula (I) to precipitate said compound; and
(vi) separating the precipitated compound of formula (I).

Where Z in the compounds of formula (I) and (II) represents a group of formula

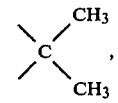

the compound of formula (I) obtained by the process of the invention is a penicillin derivative of formula (Ia):

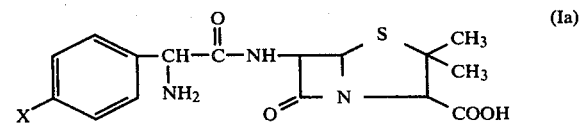

(Ia)

(in which X is as defined above).

Where Z in said compounds of formula (I) and (II) represents a group of formula

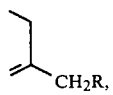

the compound of formula (I) is a cephalosporin derivative of formula (Ib):

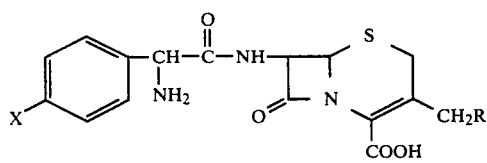

(in which R and X are as defined above).

The invention is further illustrated by the following Examples.

EXAMPLE 1

20.4 g of triethylamine were added, at 10° C., to a mixture of 21.6 g of 6-aminopenicillanic acid and 350 ml of methylene chloride. The mixture was stirred for 30 minutes and then 22 g of chlorotrimethylsilane were added dropwise, maintaining the temperature at 10° C.

The mixture was then warmed to 20° C. and stirred at that temperature for 1 hour. At the end of this time, 10 g of N-methylpyrrolidone were added and the mixture was then cooled to 5° C. 21 g of D(−)-phenylglycyl chloride hydrochloride were added all at once and the stirring was continued at the same temperature for 2 hours. 250 ml of water were then added over a period of 5 minutes and the organic phase was separated and discarded. The pH of the aqueous phase was adjusted to a value of 4.5 by the addition of aqueous ammonia. The mixture was then stirred for 4 hours at 5° C., after which the precipitate obtained was filtered off, washed with water and dried to give 24.5 g of pure ampicillin trihydrate. The purity, determined by iodometric assay against an authentic sample, was 101.5%.

$[\alpha]^{20}_D = 296.3°$ (c=0.25, H$_2$O).

Water content, Karl Fischer (KF)=13.1%.

EXAMPLE 2

The procedure described in Example 1 was repeated, except that 19.8 g of N-methylpyrrolidone were used, giving 27.8 g of pure ampicillin trihydrate.

EXAMPLE 3

The procedure described in Example 2 was repeated, except that the chlorotrimethylsilane was replaced by 47.5 g of tributylchlorosilane. 27.4 g of pure ampicillin trihydrate were obtained.

EXAMPLE 4

The procedure described in Example 2 was repeated, except that the D(−)-phenylglycyl chloride hydrocholoride was replaced by 24 g of D(−)-p-hydroxyphenylglycyl chloride hydrochloride; 29.1 g of amoxycillin trihydrate were obtained. Iodometric assay against an authentic sample showed the product to have a purity of 102.1%.

$[\alpha]^{20}_D = 299.4°$ (c=0.2, H$_2$O).

Water content, KF=12.4%.

EXAMPLE 5

30.6 g of triethylamine were added at 5° C. to a mixture of 32.4 g of 6-aminopenicillanic acid and 500 ml of methylene chloride. After leaving the mixture for 45 minutes, 35 g of dichlorodimethylsilane were added dropwise. The reaction mixture was allowed to warm to 25° C. and was stirred at this temperature for 1.5 hours. The mixture was then cooled to 0° C. and 31.2 g of N-methylpyrrolidone were added, followed by 33 g of D(−)-p-hydroxyphenylglycyl chloride hydrochloride. Stirring was continued at 0° C. for 2 hours, and then 380 ml of water were added. The mixture was then worked up as described in Example 1, giving 42.8 g of amoxycillin trihydrate.

EXAMPLE 6

The procedure described in Example 5 was repeated, except that the dichlorodimethylsilane was replaced by 42.6 g of dichlorodiethylsilane, yielding 42.6 g of amoxycillin trihydrate.

EXAMPLE 7

The procedure described in Example 5 was repeated, except that the D(−)-p-hydroxyphenylglycyl chloride hydrochloride was replaced by 32.5 g of D(−)-phenylglycyl chloride hydrochloride, yielding 40.6 g of ampicillin trihydrate.

EXAMPLE 8

42.3 g of 6-aminopenicillanic acid were suspended in 300 ml of acetonitrile, and then 34.4 g of hexamethyldisilazane were added to the suspension. The mixture was heated to 60° C. under a nitrogen atmosphere for 1.5 hours and then cooled at 10° C. At this time, 40 g of N-methylpyrrolidone were added, followed by 43.0 g of D(−)-p-hydroxyphenylglycyl chloride hydrochloride. The mixture was stirred for 3 hours at 10° C. and then 700 ml of water were added. Sufficient aqueous ammonia was then added to adjust the pH to 5 and the mixture was stirred at 10° C. for 5 hours. The precipitate was filtered off and washed with water, yielding 51.7 g of amoxycillin trihydrate.

EXAMPLE 9

The procedure described in Example 8 was repeated, except that the D(−-)-p-hydroxyphenylglycyl chloride hydrochloride was replaced by 40.1 g of D(−)-phenylglycyl chloride hydrochloride. 50.1 g of ampicillin trihydrate were obtained.

EXAMPLE 10

The procedure described in Example 7 was repeated, except that the N-methylpyrrolidone was replaced by 49.5 g of N-n-propylpyrrolidone. The yield of ampicillin trihydrate was 49.7 g.

EXAMPLE 11

21.4 g of 7-aminodesacetoxycephalosporanic acid were suspended in 450 ml of acetonitrile, and then 17.7 g of hexamethyldisilazane were added to the suspension. The mixture was heated to 65° C. for 2 hours under a nitrogen atmosphere and then cooled to 15° C. 22 g of N-methylpyrrolidone were added. After 10 minutes, 22.5 g of D(−)-phenylglycyl chloride hydrochloride were added and the mixture was stirred at 15° C. for 4 hours and then added to 500 ml of water at 10° C. Aqueous ammonia was then added to the reaction mixture to precipitate the desired product which, after 10 hours, was filtered off and dried. 25 g of cephalexin [7-(D-α-aminophenylacetamido)desacetoxycephalosporanic acid] were obtained. Iodometric assay against an authentic sample showed that the product was 98.7% pure.

EXAMPLE 12

30.6 g of triethylamine were added at 5° C. to a mixture of 32.2 g of 7-aminodesacetoxycephalosporanic acid and 600 ml of methylene chloride. After 45 minutes, 35 g of dichlorodimethylsilane were added dropwise and then the reaction mixture was allowed to warm to 25° C. and stirred for 1.5 hours. The mixture was then cooled to 0° C. and 31.2 g of N-methylpyrrolidone were added, followed by 33 g of D(−)-p-hydroxyphenylglycyl chloride hydrochloride. Stirring was continued at 0° C. for 2.5 hours, and then 450 ml of water were added. The aqueous and organic phases were separated and the pH of the aqueous phase was gradually raised to about 5 by addition of aqueous ammonia. The mixture obtained was then stirred for 12 hours and the precipitate was filtered off to give 41.5 g of cephadroxyl [7-(D-2-amino-2-p-hydroxyphenylacetamido)desacetoxycephalosporanic acid]. Iodometric assay of this product against an authentic sample showed it to be 98.2% pure.

EXAMPLE 13

The procedure described in Example 12 was repeated, except that the 7-aminodesacetoxycephalosporanic acid was replaced by 40.9 g of 7-aminocephalosporanic acid and the D(−)-p-hydroxyphenylglycyl chloride hydrochloride was replaced by 30.6 g of D(−)-phenylglycyl chloride hydrochloride. 44.3 g of cephaloglycin were obtained and were shown by iodometric assay to be 99.6% pure.

EXAMPLE 14

A mixture of 4.7 g of 7-amino-3-(1,2,3-triazol-4-yl)thiomethyl-3-cephem-4-carboxylic acid, 100 ml of methylene chloride and 3.1 g of triethylamine was silylated with 3.5 g of dichloromethylsilane. 3.5 g of N-methylpyrrolidone were then added, followed by 3.3 g of D(−)-p-hydroxyphenylglycyl chloride hydrochloride. The mixture was then worked up as described in Example 12, giving 5.2 g of cephatrizine [7-(D-2-amino-2-p-hydroxyphenylacetamido)-3-(1,2,3-triazol-4-yl)thiomethyl-3-cephem-4-carboxylic acid] of 97.1% purity.

I claim:

1. A process for preparing compounds of formula (I):

[structure of formula (I)]

[in which:
Z represents a group of formula $\diagdown C \diagup^{CH_3}_{CH_3}$ or $\diagup\diagdown_{CH_2R}$ ;

R represents a hydrogen atom, a 1-pyridyl group or a group of formula —YR' (in which: R' represents an alkyl group, an alkanoyl group, a carbamoyl group or a heterocyclic group; and Y represents an oxygen or a sulphur atom);

X represents a hydrogen atom or a hydroxy group; and the α-amino acid moiety is in the D(−)configuration] which comprises:

(a) silylating a compound of formula (II):

[structure of formula (II)]

(in which Z is as defined above);

(b) acylating the product of step (a) with D(−)-phenylglycyl chloride hydrochloride or with D(−)-p-hydroxyphenylglycyl chloride hydrochloride in the presence of an N-alkylpyrrolidone, the molar ratio of said N-alkylpyrrolidone to said compound of formula (II) being from 1:1 to 4:1; and (c) hydrolyzing the product of step (b) to give said compound of formula (I).

2. A process according to claim 1, in which the silylating agent employed in step (a) is an alkylchlorosilane, an alkoxychlorosilane or a hexaalkyldisilazane.

3. A process according to claim 2, in which the or each alkyl group in said silylating agent has from 1 to 4 carbon atoms and, where said silylating agent contains two or more alkyl groups, the alkyl groups are the same.

4. A process according to claim 3, in which said silylating agent is a trialkylchlorosilane.

5. A process according to claim 4, in which said trialkylchlorosilane is chlorotrimethylsilane.

6. A process according to claim 3, in which said silylating agent is a dialkyldichlorosilane.

7. A process according to claim 6, in which said dialkyldichlorosilane is dichlorodimethylsilane.

8. A process according to claim 3, in which said silylating agent is hexamethyldisilazane.

9. A process according to claim 2, in which said silylating agent is chlorotriethoxysilane.

10. A process according to claim 1, in which said N-alkylpyrrolidone is N-methylpyrrolidone.

11. A process according to claim 1, in which said ratio of said N-alkylpyrrolidone to said compound of formula (II) is from 1.8:1 to 2.2:1.

12. A process according to claim 1, effected in the presence of an inert organic solvent.

13. A process according to claim 12, in which said solvent is a chlorinated hydrocarbon.

14. A process according to claim 13, in which said chlorinated hydrocarbon is methylene chloride.

15. A process according to claim 12, in which said solvent is acetonitrile.

16. A process according to claim 1, in which the hydrolysis in step (c) is effected by adding water to the reaction mixture and the organic phase is, if necessary, then separated.

17. A process according to claim 1, in which, after step (c) the pH of the reaction mixture is adjusted to or to approximately the isoelectric point of said compound of formula (I) to precipitate said compound (I), which is then separated from the reaction mixture.

18. A process according to claim 1, in which Z in said compound for formula (II) represents a group of formula

to produce a compound of formula (Ia):

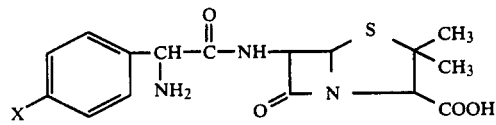

(in which X is as defined in claim 1).

19. A process according to claim 1, in which Z in said compound of formula (II) represents a group of formula

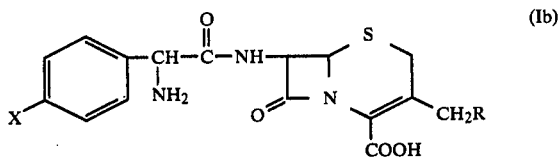

(in which R is as defined in claim 1) to produce a compound of formula (Ib):

(Ib)

(in which X and R are as defined in claim 1).

20. A process according to claim 19, applied to the production of cephalexin, cephadroxyl, cephaloglycin or cephatrizine.

* * * * *